United States Patent [19]

Falk

[11] Patent Number: 4,896,549
[45] Date of Patent: Jan. 30, 1990

[54] MOLTEN METAL SAMPLER

[76] Inventor: Richard A. Falk, 122 Nurmi Dr., Fort Lauderdale, Fla. 33301

[21] Appl. No.: 205,464

[22] Filed: Jun. 10, 1988

[51] Int. Cl.$^4$ .......................... G01N 1/12; G01K 1/12
[52] U.S. Cl. .................................. 73/864.53; 374/140
[58] Field of Search ................. 73/864.52–864.59, 73/DIG. 8; 136/234; 374/26, 139, 140; 266/99; 204/400

[56] References Cited

U.S. PATENT DOCUMENTS

| | | |
|---|---|---|
| 2,999,121 | 9/1961 | Mead . |
| 3,246,520 | 4/1966 | Gaskill et al. ................. 136/234 |
| 3,357,250 | 12/1967 | Lowdermilk ................. 73/DIG. 9 |
| 3,503,259 | 3/1970 | Carlson et al. ................. 73/DIG. 9 |
| 3,619,381 | 11/1971 | Fltterer . |
| 3,693,449 | 9/1972 | Collins ................. 73/DIG. 9 |
| 3,748,908 | 7/1973 | Falk . |
| 3,753,372 | 8/1973 | Collins ................. 73/DIG. 9 |
| 3,791,219 | 2/1974 | Falk . |
| 3,915,002 | 10/1975 | Hanle et al. ................. 73/DIG. 9 |
| 3,967,505 | 7/1976 | Feichtinger . |
| 4,051,732 | 10/1977 | Falk . |
| 4,069,715 | 1/1978 | Falk . |
| 4,326,426 | 4/1982 | Falk . |
| 4,358,630 | 11/1982 | Falk . |
| 4,503,716 | 3/1985 | Wuensch . |
| 4,535,640 | 8/1985 | Falk . |
| 4,659,679 | 4/1987 | Falk . |
| 4,699,014 | 10/1987 | Boron . |

Primary Examiner—Robert R. Raevis
Attorney, Agent, or Firm—Fuller, Puerner & Hohenfeldt

[57] ABSTRACT

A molten metal sampler includes an insulative pod which is joined to a paperboard sleeve which is connected to the metal handle. The pod is molded from a refractory composition and surrounds the tube and has an integral pocket to support any of a wide variety of sample molds or form a sample or mold a sample within itself adjacent to the tube. The cardboard tube can carry a heat sensor or oxygen sensor. The pod can contain a separate measuring device which can measure the cooling curve of the sample in the pod.

7 Claims, 1 Drawing Sheet

U.S. Patent
Jan. 30, 1990
4,896,549
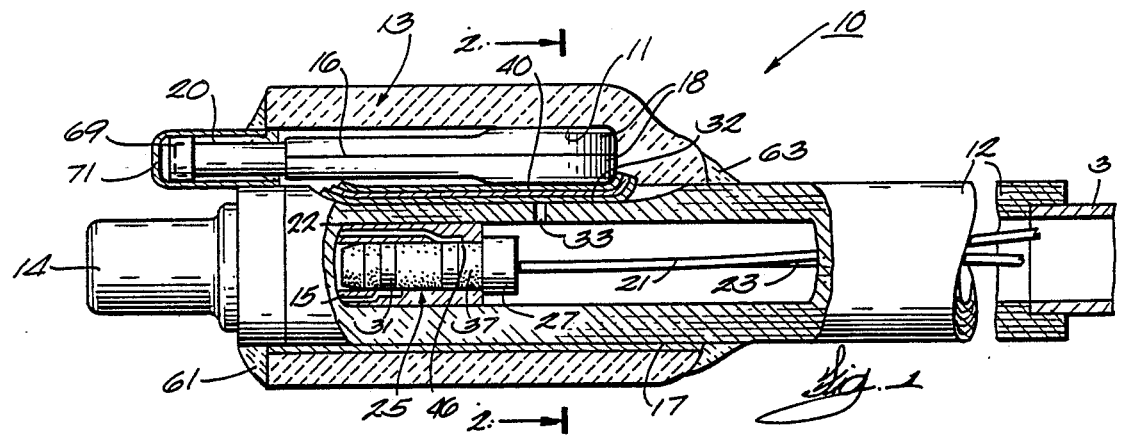
Fig. 1
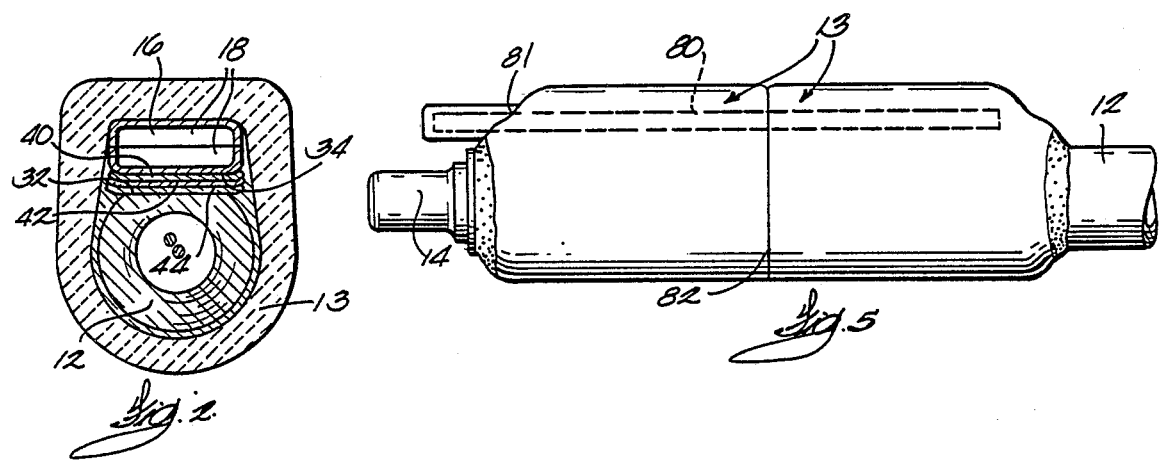
Fig. 2
Fig. 5
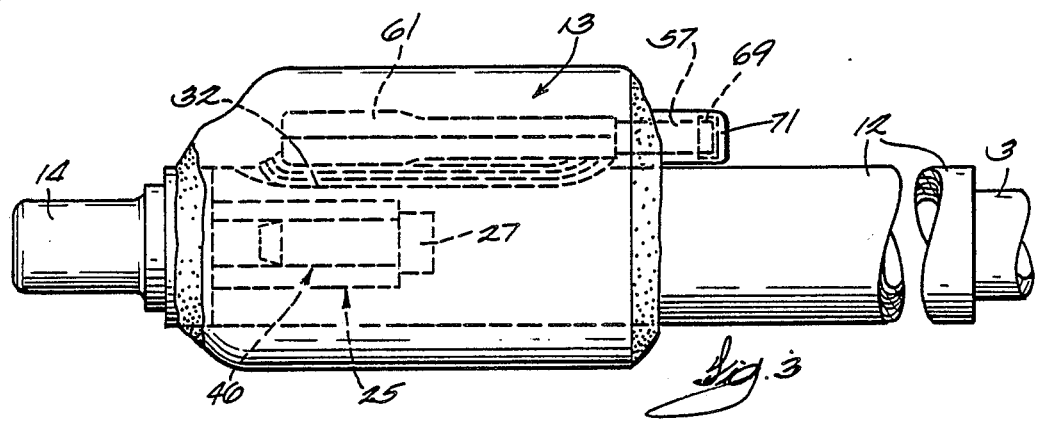
Fig. 3
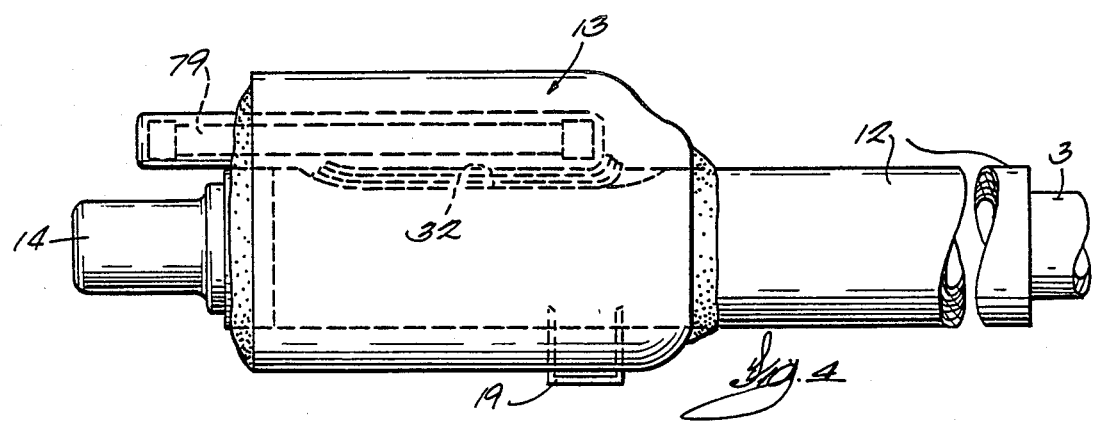
Fig. 4

MOLTEN METAL SAMPLER

BACKGROUND OF THE INVENTION

The invention relates to molten metal sampling apparatus and is a further development of the subject matter of my U.S. Pat. Nos. 4,069,715 and 4,535,640. The prior art U.S. Pat. No. 4,069,715 shows a piggyback arrangement for joining two cardboard instrument carrying sleeves with refractory cement and staples or the like in side by side relationship to enable immersion in molten metal of the two side by side tubes to simultaneously obtain a metal sample and a bath temperature. This affords the opportunity of obtaining a bath temperature measurement with the thermocouple and also retrieving a sample of molten metal from the bath from a point adjacent to the sensor of the thermocouple with two independent pieces of equipment integrated together using one immersion tube. It is known to use combination samplers and thermocouples. U.S. Pat. No. 4,699,014 is an example of this art. These samplers are limited somewhat to the sample shapes and sizes of samples which can be confined and arranged in a workable fashion in one housing.

Although the apparatus disclosed in U.S. Pat. No. 4,069,715 was effective to accomplish the intended results it was never commercialized because there was no major cost saving as compared to using separate thermocouple tubes and separate sampling lances containing sample retrieving equipment. These piggyback samplers also had a large mass and displaced a large quantity of molten metal and were inconvenient to use and there was no quick sample release. They were not non-boiling and a large quantity of paperboard was exposed to the melt and gasified causing metal splash.

A large number of samplers presently include a heat sensor or thermocouple as well as a mold for molding a sample. Complex and expensive arrangements are required to isolate the molten metal from the cold junction of the thermocouple wires and the lead wires. The cold junction must also be isolated from the heat of the metal bath and the internally located hot sample. These samplers are difficult and time consuming to take apart for retrieval of the sample. In view of the fact that a great number of measurements are repeatedly taken in steel mills there is a need for low cost and easy to use sampling equipment because normally the sampler and sensor are consumed and not available for repetitive use. Accordingly, cost savings, safety and time and speed of operation are major factors in the construction of molten metal sampling equipment.

SUMMARY OF THE INVENTION

The invention provides a structural and insulative shell or pod width a pouch for carrying metal sampling equipment in adjacent relationship to a tube for supporting an oxygen sensor or thermocouple. The pod is more compact and safe to use than the piggyback sampler mentioned above and provides an inexpensive combination of sampler and sensor with good isolation and insulation for the cold junction of the heat sensor. The pod is provided with an inside arcuate surface which forms a sleeve slightly larger in diameter than the cardboard tubes typically employed for immersion thermocouples or oxygen sensors. The pod snugly receives the outside surface of the tube. These cardboard tubes typically have an outside diameter of around 1½" but can be larger or smaller. At one side of the pod the arcuate walls merge with flat walls which form a channel pocket or pouch which is open at one end and open facing the cardboard tube. The pocket is adapted to receive and support a variety of molten metal samplers in close proximity to the sensor tube. The pod and pouch can be downwardly open or upwardly open with the fill tubes for the sampler either projecting upwardly or downwardly depending on the characteristics of the sample being taken. With high temperature molten metal, the sample metal tends to run out of the fill tube during retrieval of the sample from the bath. The open ends of two pods can face each other in mouth to mouth or allochiral relation to accommodate large sample molds. The pods are easily shaped to provide openings and compartments such as a mixing chamber to mix molten metal with a de-oxidant before it enters the sample mold.

The pod is desirably made from a non-boiling substance such as those disclosed in my U.S. Pat. Nos. 4,659,679 and 4,535,640, the entire disclosure of which is incorporated herein by reference. These patents disclose use of a refractory fiber such as Babcok and Wilcox's Kaowool 2600 bulk fiber alone or with other ingredients as disclosed therein. The non-boiling characteristics of a pod made in accordance with the compositions disclosed in those patents ensures that there is no carbon from combusting paperboard added to the sample retrieved by the molten metal sampler caused by combustion of the cardboard tube as could occur with U.S. Pat. No. 4,069,715. Thus the sampler of the invention is particularly desirable in measuring a low carbon content of a melt which could be effected by combustion of cardboard materials.

Moreover, the pod protects the cardboard tube which supports the thermocoupler oxygen sensor and shields it from the molten metal bath. This protects the cold junction of the thermocouple wires and the leads therefor to prevent the generation of a false emf which could affect the accuracy of the temperature measurement. In addition, the pod protects the molten metal sampler metal mold parts from the melt so they are not melted or covered with molten metal which can interfere with retrieval of the sample from the interior of the mold parts.

The pod is desirably secured in place on the handle by refractory cement at both ends and between the pod walls and the support tube. A staple through the pod and into the cardboard tube can also be employed. The refractory cement also seals the silica sand which is mixed with sodium silica fill which can be employed to pack the sampler in the sampler pouch or pocket.

The cardboard tube can be fitted with a dummy sensor and dummy connecting plug. The plug can be of the type illustrated in various thermocouple patents including U.S. Pat. No. 3,748,908 incorporated by reference herein to connect the electric socket to the jack in the tube to hold the pod to the cardboard tube during use.

One or more pods can be connected to a tube. Also, a heat sensor can be used to measure the cooling curve of a sample in a pod cavity.

Further objects, advantages, and features of the invention will become apparent from the disclosure.

DESCRIPTION OF THE DRAWINGS

FIG. 1 is a fragmentary sectional view of a sampler in accordance with the invention.

FIG. 2 is a sectional view along line 2—2 of FIG. 1.

FIG. 3 is a view of modified embodiment of the sampler.

FIG. 4 is a view of a further modified embodiment with an evacuated hydrogen sample tube.

FIG. 5 is a view on reduced scale of an assembly of two pods.

DESCRIPTION OF PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

FIG. 1 shows a molten metal sampling apparatus 10 which includes a paperboard support tube 12 which may be provided with a conventional thermocouple assembly 14 or conventional oxygen sensor 14. In accordance with the invention an insulative pod 13 is attached to the tube 12 by refractory cement 17 and 61. A staple 19 (FIG. 4) can also be employed. A molten metal sampler 16 formed from two metal mold halves 18 is provided with a fused quartz fill tube 20. The metal sampler molds fit in a pouch 11 in the pod 13. The pouch 11 is molded in place at the time of molding the pod and is in offset relation to the curved or arcuate internal pod surfaces which embrace the curved surface of the tube 12.

A thermocouple assembly 14 can be of the type illustrated in my U.S. Pat. No. 4,358,630 or U.S. Pat. No. 2,999,121 the entire disclosures of which are incorporated herein by reference. The oxygen sensor can be in accordance with the disclosure in the Fritter Patent, U.S. Pat. No. 3,619,381.

The thermocouple wires 22 and 15 are connected to leads 21, 23 on plug 27 fixed in tube 12 by contacts 31, 37 in the socket which form a cold junction 46.

The molds for retrieving a sample of molten metal can be of various convention types including those illustrated in U.S. Pat. Nos. 3,791,219, 4,051,732, 4,326,426 or 4,503,716 the entire disclosures of which are incorporated herein by reference. The mold can also be a cavity formed in the pod and lined or unlined with metal or refractory.

To make the pod more compact the cylindrical side wall of the cardboard tube can be shaved or cut to form a flat 32 at a location opposite the sample mold.

Between the metal flat 34 of the sample mold and the cardboard tube flat 32 an insulative lamina is provided which includes a refractory blanket 40 and a layer of aluminum foil 42 and a second sheet of refractory blanket 44. This lamina is desirably provided to isolate and insulate the molten metal from the cardboard tube to avoid heating the cold junction 46 of the thermocouple which heat could interfere with temperature measurements with the thermocouple heat sensor. The refractory blanket can be made from Kaowool 2600 described above.

The flat 32 aids in positively positioning the flat adjacent sampler surface 34 in the sampler. The flat 32 is spaced from the flat 34 to snugly receive and position the sample mold halves 18 when provided with or without the insulating lamina which is not required in all combinations.

A vent hole 33 is desirably employed in the paperboard tube adjacent the pouch to afford venting of air from the pouch to allow the air to escape to assist in the filling of the mold by the incoming molten metal. The insulation acts as a filter to remove some of the tars which evolve from the sample and which can deposit on the metal pipe or handle 3 which is connected to the cardboard tube. Accumulations of deposits on the pipe can interfere with repetitive assembly of samplers on the pipe.

Refractory cement at 61 and 63 seal the pod to the tube 12 and the samplers in the pouch. A sand fill or refractory fiber packing can also be employed to pack small sample molds in the pouch 11.

FIG. 3 shows a sampler with the fill tube 57 extending upwardly to prevent loss of the metal fill from the sampler 61. Where the metal is hot or of high fluidity, the FIG. 1 arrangement can lose metal when the sampler is retrieved and before the sample cools. In FIG. 1 the fill tube 20 is downwardly open. Fusible caps 69 and 71 are used to seal the mold cavity when moving the samples through the slag.

In FIG. 4 the pocket is provided with an elongated evacuated hydrogen sampler tube assembly 79 which can be of the type disclosed in U.S. Pat. No. 3,967,505, the entire disclosure of which is incorporated by reference.

FIG. 5 shows an assembly of two pods with the pockets in mouth to mouth relation which can thus accommodate a larger sampler 80. An opening 81 is formed in the relatively soft pod by punching or drilling. Although in the disclosed embodiments the pods are molded from an insulative refractory fiber composition, other materials could be employed to obtain some of the advantages of the invention, including paper, ceramic, wood, or metal, etc. The pods can be cemented together at the seam 82.

I claim:

1. Apparatus for measuring properties of molten metal comprising:
   an elongated tube adapted to be connected to a handle for manipulation thereof,
   a first molten metal measurement device supported by said tube,
   a second molten metal measurement device,
   a pod for receiving said second measurement device in embracing contact laterally along side said tube and first molten metal measuring device, and said pod having wall means defining a tube sleeve portion which interfits with said tube to support the pod on said tube, the pod wall means defining a pouch to receive said second measurement device, and means for securing said second molten metal measurement device in said pouch, said pod having common wall means surrounding and forming said pouch and said tube sleeve portion.

2. The apparatus of claim 1 wherein said tube sleeve portion is open to said pouch to form a common chamber.

3. The apparatus of claim 2 wherein said tube is provided with a flat adjacent said pouch to positively position an adjacent flat of the second molten metal measurement device.

4. Apparatus of claim 1 wherein said wall means has a curved inside surface complementary to the surface of said tube with the curved surface merging with flat surfaces which form a generally rectangular channel for receiving the second molten metal measurement device.

5. The apparatus of claim 1 wherein the tube defines a vent hole for connecting the interior of the tube with the pouch to thereby allow air to escape from the pouch to the tube interior during use.

6. Apparatus for measuring properties of molten metal comprising handle means for supporting a thermocouple having a cold junction, an insulative pod adapted to be connected to the handle means for manipulation thereby in a molten metal bath and said pod including wall means defining a common chamber having a curved portion for receiving the handle means and an offset pouch, said pouch being dimensioned to receive and support in offset relationship from the handle means and the thermocouple a molten metal sampler having a mold, and insulative means between the thermocouple and the pouch to insulate said cold junction of the thermocouple from heat in the molten metal sampler in the pouch.

7. The apparatus of claim 6 wherein said insulative means between the pouch and said cold junction comprises a lamina of refractory fiber and a metallic sheet.

* * * * *